United States Patent [19]
Otsuka et al.

[11] Patent Number: 4,786,395
[45] Date of Patent: Nov. 22, 1988

[54] OXYGEN ANALYZER

[75] Inventors: Shinya Otsuka, Shita; Zensaku Kozuka, Takatsuki, both of Japan

[73] Assignee: Toray Industries, Inc., Tokyo, Japan

[21] Appl. No.: 803,288

[22] PCT Filed: Mar. 6, 1985

[86] PCT No.: PCT/JP85/00111

§ 371 Date: Nov. 7, 1985

§ 102(e) Date: Nov. 7, 1985

[51] Int. Cl.$^4$ .............................................. G01N 27/46
[52] U.S. Cl. ..................... 204/409; 204/1 T; 204/421; 204/424
[58] Field of Search ............... 204/1 S, 421–429, 204/409

[56] References Cited

U.S. PATENT DOCUMENTS

| | | | |
|---|---|---|---|
| 3,051,643 | 8/1962 | Bergson | 204/430 |
| 3,081,250 | 3/1963 | Hall et al. | 204/430 |
| 3,661,724 | 5/1972 | Strickler | 204/430 |
| 3,699,032 | 10/1972 | Rapp | 204/1 S |
| 3,819,499 | 6/1974 | Hoogeveen et al. | 204/1 S |
| 3,933,429 | 1/1976 | Shibata et al. | 204/427 |
| 4,128,458 | 12/1978 | Obiaya | 204/1 S |
| 4,169,769 | 10/1979 | Capone | 204/1 S |
| 4,312,733 | 1/1982 | Ninomiya et al. | 204/424 |
| 4,539,086 | 9/1985 | Fujita et al. | 204/427 |

OTHER PUBLICATIONS

*Journal of Electrochemical Society,* May, 1969, pp. 594–600.

*Transactions of the Japan Institute of Metals,* vol. 25, No. 9 (1984), pp. 639–648.

Primary Examiner—T. Tung
Attorney, Agent, or Firm—Birch, Stewart, Kolasch & Birch

[57] ABSTRACT

An electrochemical oxygen pump utilizing a solid electrolyte is provided on a closed gas flow path in which a carrier gas is circulated. By applying a constant direct current voltage to the oxygen pump, the oxygen in the carrier gas is pumped-out and discharged from the path to the atmosphere so that the oxygen partial pressure in the closed gas flow path is held at a sufficiently low and constant value. Under this state, a sample containing oxygen is charged into the closed gas flow path. Then, the oxygen content in the sample can be determined by measuring the quantity of electricity which passes through the oxygen pump during pumping of the oxygen released from the sample. Under this arrangement, the oxygen content in samples of metals, alloys, metal compounds, metalloids or gases can be determined as absolute values rapidly and accurately.

5 Claims, 11 Drawing Sheets

OXYGEN ANALYZER

FIELD OF THE INVENTION

The present invention relates to an oxygen analyzer and an oxygen analyzing method, and more specifically to a device and a method capable of measuring the oxygen content in metals and alloys (both referred to as metals hereinafter) and metal compounds, and metalloids (e.g. selenium, tellurium), or in gases.

BACKGROUND OF THE INVENTION

Recently, metals, metal compounds and metalloids have drawn attention as materials for use in various functional mechanisms and electronic devices. A reduction of impurities contained in these materials is desired because of the increase in performance characteristics now necessary. The same situation exists on oxygen content, and various devices to measure oxygen content or oxygen concentration in materials have been used pursuant to the increasing necessity of the reduction of impurities. Various devices have been used for the measurement of oxygen content or oxygen concentration in gases.

Two types of devices exist to measure the oxygen content or concentration in these materials or gases. One type of the devices measures the oxygen content or the oxygen concentration as an absolute value and the other type of device measures the oxygen content or the oxygen concentration as a relative value.

However, the device which measures absolute value involves not only complicated handling but also takes a long time to complete a measurement.

As the device which measures the relative value, there is in practical use, for instance, a device in which the oxygen contained in a sample or a gas is converted to carbon monoxide through a reaction with carbon, the carbon monoxide is changed to carbon dioxide by the use of an appropriate reagent and thereafter the quantity of the carbon dioxide is measured by infrared absorption or heat conduction. Since such a device yields a relative value, it always requires standard samples. Therefore, when the device is employed, the measured results can be wrong due to an error in the preparation of the standard samples. Moreover, in the range of a low oxygen concentration, the standard samples are difficult to prepare, and thus the measured results obtained by the device lack reliability.

Therefore, the object of the present invention is to provide an oxygen analyzer and an oxygen analyzing method which are free from the above-mentioned drawbacks of the conventional devices and can make a rapid and precise measurement of an oxygen content as an absolute value even in the range of a low oxygen concentration.

SUMMARY OF THE INVENTION

To accomplish the above-mentioned object, an oxygen analyzer according to the present invention is constructed as follows:

1. An oxygen analyzer comprising:
 (a) a closed gas flow path having a carrier gas inlet port, a vacuum formation port and a sample-introducing port;
 (b) a circulation pump for circulating a carrier gas and an electrochemical oxygen pump utilizing a solid electrolyte, the circulation pump and the electrochemical oxygen pump being provided in series on the closed gas flow path;
 (c) a set of lead wires connected to the oxygen pump;
 (d) means for applying a direct current voltage connected to the lead wires; and
 (e) at least one measuring means connected to the lead wires, the measuring means being selected from a means for measuring an electric current and a means for measuring a quantity of electricity.

2. An oxygen analyzer comprising:
 (a) a closed gas flow path having a carrier gas inlet port, a vacuum formation port and a sample-introducing port;
 (b) a circulation pump for circulating a carrier gas and an electrochemical oxygen pump utilizing a solid electrolyte, the circulation pump and the electrochemical oxygen pump being provided in series on the closed gas flow path;
 (c) a sample-melting furnace provided on the closed gas flow path downstream of the sample-introducing port and upstream of the oxygen pump as viewed along the carrier gas flow;
 (d) a set of lead wires connected to the oxygen pump;
 (e) means for applying a direct current voltage connected to the lead wires; and
 (f) at least one measuring means connected to the lead wires, the measuring means being selected from a means for measuring an electric current and a means for measuring a quantity of electricity.

In the above analyzers, the following additional features may be adopted:

The oxygen analyzer of 1, has a filter provided on the closed gas flow path downstream of the sample-introducing port and upstream of the oxygen pump, as viewed along the carrier gas flow.

The oxygen analyzer of 2 has a cooling means provided so as to surround the closed gas flow path downstream of the sample-melting furnace and upstream of the oxygen pump, as viewed along the carrier gas flow.

The oxygen analyzer of 2 has a filter is provided on the closed gas flow path downstream of the sample-melting furnace and upstream of the oxygen pump, as viewed along the carrier gas flow.

The oxygen analyzer of 2 has a filter provided on the closed gas flow path downstream of the cooling means and upstream of the oxygen pump, as viewed along the carrier gas flow.

In the oxygen analyzer of 1 or 2, the oxygen pump comprises a heating furnace, a cylindrical solid electrolyte housed in the heating furnace and porous electrodes provided inside and outside of the solid electrolyte.

The solid electrolyte comprises a zirconia material stabilized with one oxide selected from 5–15 mol % calcium oxide, 6–10 mol % magnesia and 4–12 mol % yttria.

The solid electrolyte comprises a zirconia material stabilized with at least two oxides selected from 5–20 mol % calcium oxide, 5–20 mol % magnesia and 5–20 mol % yttria.

The solid electrolyte comprises a thoria stabilized with 4–25 mol % yttria.

A rectifying tube fabricated of a heat-proof material is placed inside of the solid electrolyte.

The rectifying tube is formed in a capsule-shape and the tube is made into a vacuum.

In the oxygen analyzer of 1 or 2, the oxygen pump has a further set of lead wires connected thereto, the further set of lead wires being connected to a means for measuring direct current voltage.

In the oxygen analyzer of 1 or 2, the direct current voltage applying means is a direct current power source with a variable voltage.

Since a closed gas flow path is used, the oxygen pump with the lead wires is provided on the path, and the lead wires are connected to the direct current voltage applying means, the oxygen partial pressure, namely, the oxygen chemical potential at the interface between the solid electrolyte in the oxygen pump and the closed gas flow path, can be held constant, by applying a constant direct current voltage to the oxygen pump. Before introducing the sample and measuring the oxygen content in the sample, the oxygen in the carrier gas in the closed gas flow path is extracted by the oxygen pump. Since the oxygen partial pressure at the interface of the solid electrolyte is maintained constant, after extracting the oxygen from the carrier gas, the oxygen partial pressure thereof also reaches a sufficiently low, constant value in equilibrium and maintains its state, under the condition including the effects of the specific electronic conductivity of the solid electrolyte and the effects of the oxygen released from the solid electrolyte itself, as well as the oxygen having leaked into the path from the atmosphere. Under this state, the sample is introduced into the closed gas flow path and the oxygen having been contained in the sample is released from the sample into the closed gas flow path. The oxygen released from the sample is carried by the carrier gas to the oxygen pump which extracts the oxygen from the closed gas flow path into the atmosphere. From the quantity of electricity needed for the pumping-out of the oxygen, the oxygen content in the sample can be measured.

Since the sample is introduced under the condition that the oxygen partial pressure at the interface between the solid electrolyte and the closed gas flow path is maintained constant and low, the oxygen content in the sample can be measured without being influenced from the specific electronic conductivity of the solid electrolyte, and the oxygen released from the solid electrolyte itself, as well as the oxygen having leaked into the path from the atmosphere.

As a result, the measurements have a high degree of accuracy even at an oxygen concentration lower than 1 ppm. Furthermore the measured result of the oxygen concentration can be obtained as an absolute value without using any standard sample.

In addition, the present analyzer makes it possible to measure the oxygen content as an absolute value with high accuracy, even where the melting of the samples is necessary to release the oxygen from samples such as metals, because the present analyzer is provided with a sample melting furnace downstream of the sample inlet port and upstream of the oxygen pump as viewed along the carrier gas flow. The response is fast because the melting of the sample permits the operation of the oxygen pump via a gaseous phase. Moreover, since the sample-melting temperature can be set independent of the operating temperature of the oxygen pump, the number of the types of samples that can be measured is increased.

To accomplish the aforementioned objects of the present invention, the oxygen analyzing method in accordance with the present invention is performed as follows:

(a) introducing and circulating a carrier gas in a closed gas flow path on which an electrochemical oxygen pump utilizing a solid electrolyte is provided;

(b) applying a constant direct current voltage to the oxygen pump during measuring, thereby keeping the oxygen partial pressure constant at the interface between the carrier gas and the solid electrolyte;

(c) pumping-out oxygen contained in the closed gas flow path from the closed gas flow path by means of the oxygen pump so that the oxygen partial pressure in the closed gas flow path can be held at a sufficiently low constant pressure;

(d) charging a sample into the closed gas flow path and releasing oxygen contained in the sample from the sample into the carrier gas;

(e) carrying the released oxygen to the oxygen pump by the carrier gas and discharging the released oxygen from the closed gas flow path by the oxygen pump so that the oxygen partial pressure in the closed gas flow path returns to the constant pressure;

(f) calculating the quantity of electricity needed for pumping-out oxygen from the closed gas flow path in accordance with the electric current passing through the oxygen pump during the pumping-out of the released oxygen;

(g) determining the oxygen content in the sample from the quantity of electricity, the atomic weight of oxygen and Faraday's constant.

The oxygen content in the sample estimated using the following equation:

$$Q_{ion} = x \cdot 2F/M$$
$$= \int_{t_1}^{t_2} I_{ion} \, dt$$
$$= \int_{t_1}^{t_2} (I - I_\infty) \, dt$$

where,

I is the electric current which passes through the oxygen pump;

$I_\infty$ is a constant electric current which passes through the oxygen pump when the direct current voltage is applied to the oxygen pump;

$I_{ion}$ is an ionic current due to the oxygen released from the sample when the released oxygen is pumped-out from the closed gas flow path;

$t_1$ is the time at which the oxygen pump begins to pump-out the released oxygen from the closed gas flow path;

$t_2$ is the time at which the oxygen pump completes the pumping-out of the released oxygen from the closed gas flow path;

$Q_{ion}$ is the quantity of electricity generated by the ionic current $I_{ion}$;

X is the weight of the released gas which has been pumped-out from the closed gas flow path;

F is Faraday's constant; and

M is the atomic weight of oxygen.

The closed gas flow path is made into a vacuum before introducing the carrier gas.

The oxygen pump is operated at 500°-1300° C., wherein the oxygen pump is operated at 500°-1,300° C.

The carrier gas is an inert gas containing 0.01-10% hydrogen gas or more specifically, an inert gas containing 0.05-5% hydrogen gas.

The inert gas is a member selected from the group consisting of argon, nitrogen and helium.

The carrier gas is a member selected from the group consisting of carbon monooxide and carbon dioxide.

The circulating rate of the carrier gas is 0.01–100 liters/min, and more specifically.

The circulating rate of the carrier gas is 0.1–10 liters/min.

The sample is a member selected from the group consisting of metals, metal compounds, metalloids and alloys and the sample is charged and melted in the closed gas flow path at a position upstream of the oxygen pump as viewed along the carrier gas flow. The sample also can be a gas.

In a above methods since the constant direct current voltage is applied continuously to the oxygen pump, the oxygen partial pressure at the interface between the carrier gas and the solid electrolyte can be held constant throughout the measurement. Before measuring, the oxygen in the carrier gas is extracted from the closed gas flow path into the atmosphere by the oxygen pump and the oxygen partial pressure in the closed gas flow path is maintained at a low enough and constant pressure. Under this condition, the sample is charged and the oxygen released from the sample is carried by the carrier gas to the oxygen pump and pumped-out from the closed gas flow path. Due to the extraction the oxygen partial pressure in the closed gas flow path returns to the initial constant pressure before the successive charge of the sample. The of electricity quantity due to the ionic current passing through the oxygen pump at the extraction of the released oxygen corresponds to the volume of the extracted oxygen and it becomes possible to measure with a high accuracy, as an absolute value, the oxygen which was contained in the sample from the quantity of electricity, referring to the atomic weight of oxygen and Faraday's constant.

BRIEF DESCRIPTION OF THE DRAWINGS

The present invention will become more fully understood from the detailed description given hereinbelow and the accompanying drawings.

THE BEST MODE FOR CARRYING OUT THE INVENTION

Figure 1:
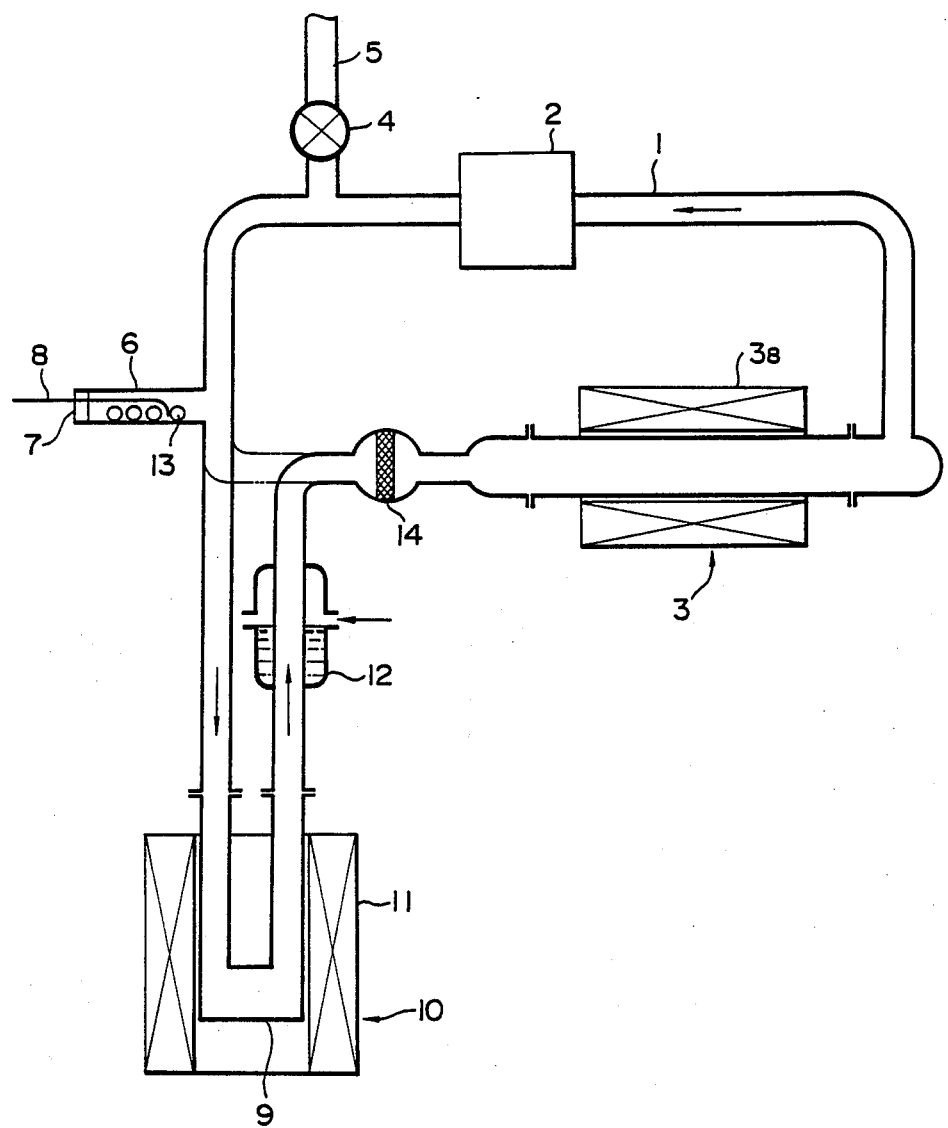
FIG. 1 is a schematic elevational view of an oxygen analyzer including the partial cross sectional view of the oxygen analyzer in a case of measuring the oxygen content in metals, in accordance with one embodiment of the present invention.

A preferred embodiment of the present invention in the case of a measurement of the oxygen content in metals will be described below. In FIG. 1, (which is an elevational view of an oxygen analyzing device of the present invention including a partial cross section thereof), on a closed gas flow path 1 which is made of a glass or metal tube and as a whole is constructed in a closed circuit, a circulation pump 2 for circulating a carrier gas and an electrochemical oxygen pump 3 (referred to as an oxygen pump hereinafter) utilizing a solid electrolyte are arranged. The oxygen pump 3 is located upstream of the circulation pump 2 as viewed along the gas flow path which is shown by the arrows in FIG. 1.

On the gas flow path 1, a pipe 5 having a valve 4 is provided downstream of the circulation pump 2. The pipe 5 functions as a carrier gas inlet port and also as a vacuum formation port. The pipe 5 is connected via a switching valve (not shown) to a carrier gas supply source and to a vacuum pump (also not shown).

Downstream of the pipe 5, a sample-charge tube 6 is connected to the closed gas flow path 1. One end of the sample-charge tube 6 is sealed with a rubber plug 7, while the other end of it opens into the closed gas flow path 1, thereby constituting the sample-introducing port. A rod 8 for introducing a sample is provided so as to penetrate the rubber plug 7.

On the closed gas flow path 1, a sample-melting furnace 10 is provided downstream of the sample-charge tube 6 and upstream of the oxygen pump 3 as viewed along the gas flow path. The sample-melting furnace 10 comprises a U-shaped tube-like sample-melting chamber 9 of a heat-proof material (such as a silica) and a heating furnace 11.

Downstream of the sample-melting furnace 10 as viewed along the gas flow path, a cooling water jacket 12 surrounding the closed gas flow path 1 as a cooling means may be provided if necessary.

Filter 14 is provided downstream of the sample-melting furnace 10 and upstream of the oxygen pump 3, in this embodiment, between the cooling water jacket 12 and the oxygen pump 3, as viewed along the gas flow path. The filter 14 may be constructed of a glass wool, a porous glass or ceramics.

Figure 2:
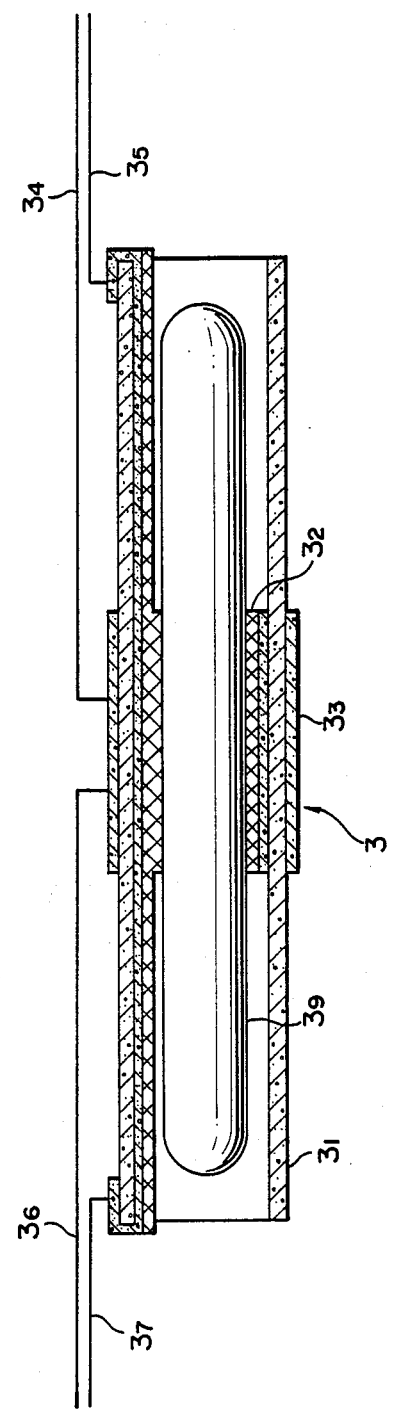
FIG. 2 is a longitudinal section of the electrochemical oxygen pump of FIG. 1 using a solid electrolyte.

The above-mentioned oxygen pump 3 has a heating furnace $3_8$ and a cylindrical solid electrolyte $3_1$ (shown in FIG. 2) housed in the heating furnace $3_8$. The solid electrolyte $3_1$ consists of a zirconia material which has been stabilized with solid solutions of oxides such as calcium oxide, magnesia and yttria, and posseses an oxygen ion conductivity. The amount of the oxide solid solution is 5–15 mol % for the calcium oxide, 6–10 mol % for the magnesia and 4–12 mol % for the yttria. Two different types of solid solutions to an extent of 5–20 mol % may be used. A solid electrolyte which consists of a thoria with a solid solution of 4–25 mol % yttria may be used. The solid electrolyte $3_1$ holds a rectifying tube $3_9$ therein which is made of a heat-proof material such as a silica and formed as a capsule with a vacuum therein.

Porous electrodes $3_2$ and $3_3$ are provided at the inside and outside surfaces of the solid electrolyte $3_1$ respectively. One portion of the inside electrode $3_2$ extends to both longitudinal ends of the electrolyte $3_1$ and is turned back to the outside surface of the electrolyte $3_1$ at the ends of the electrolyte. The porous electrodes $3_2$ and $3_3$ are constructed by pasting platinum on the surface of the solid electrolyte $3_1$ and baking it.

A set of lead wires $3_5$ and $3_7$ are connected to the electrode $3_2$ and another set of lead wires $3_4$ and $3_6$ are connected to the electrode $3_3$. A variable direct current power source (not shown) is connected between the lead wires $3_4$ and $3_5$, as a direct current voltage applying means. An ammeter (not shown) as a current measuring means is connected in series with the power source. Also, a voltmeter (not shown) is connected between the lead wires $3_6$ and $3_7$.

The electromotive force E of an oxygen concentration cell using a solid electrolyte is expressed by the following equation:

$$E=(RT/4F)\ln(P_1/P_2)$$

wherein,

R = the gas constant;
T = the absolute temperature of the solid electrolyte;
F = Faraday's constant;
$P_1$ = the oxygen partial pressure at one side of the solid electrolyte; and
$P_2$ = the oxygen partial pressure at the other side of the solid electrolyte.

As is easily understood from the above equation, the oxygen concentration cell using the solid electrolyte can function as an oxygen pump. In the cell, when a voltage is applied, oxygen moves from one side to the other side (vice versa) of the solid electrolyte, corresponding to the magnitude of the applied voltage and the polarity of the electrolyte. The present invention utilizes the above mentioned principle of the oxygen pump.

Next, one oxygen analyzing method in accordance with the present invention will be described together with an explanation about the operation of the above-mentioned oxygen analyzer.

First, the sample-melting chamber 9 is heated by the heating furnace 11 to a temperature above the melting point of the metal to be analyzed. Also, the solid electrolyte $3_1$ is heated to 500°–1,300° C. by the heating furnace $3_8$ of the oxygen pump 3.

Next, the valve 4 is opened and the closed gas flow path 1 is made into a vacuum through the vacuum pump. The vacuum is preferably as high as possible.

Following the vacuum formation within the closed gas flow path 1, the connection to the vacuum pump is cut and then the carrier gas is introduced into the closed gas flow path 1 through the pipe 5. Then the valve 4 is shut. Thus, the gas in the closed gas flow path 1 is displaced and filled with the carrier gas, which is an inert gas. The carrier gas is preferably argon gas with a 0.01–10% hydrogen gas content, and more preferrably argon gas with a 0.05–5% hydrogen gas content.

Next, the pump 2 circulates the carrier gas within the closed gas flow path 1. The circulation rate of the carrier gas is preferably 0.01–100 liters/min and more preferrably 0.1–10 liters/min. At the same time, an electric voltage is applied between the lead wires $3_4$ and $3_5$ so that the electromotive force generated between the lead wires $3_6$ and $3_7$ of the oxygen pump 3 becomes a constant value $E_2$, which corresponds to the sufficiently low oxygen partial pressure of the carrier gas. While this state is held, the oxygen pump 3 pumps out the oxygen in the closed gas flow path 1 to the atmosphere through the solid electrolyte. The electric current passing through the lead wires $3_4$ and $3_5$ is reduced rapidly with time and soon reaches a constant value of $I\infty$.

Next, by pushing the sample-charging rod 8, about 0.001–10 g of the metal sample 13 (FIG. 1) is dropped into the sample-melting chamber 9 and is subsequently melted. The oxygen which was contained in the metal reacts with the hydrogen in the carrier gas and produces gaseous $H_2O$. The $H_2O$ gas is filtered by the filter 14 and carried to the rectifying tube $3_9$ of the oxygen pump 3 where the gas is electrochemically decomposed at the inside surface of the solid electrolyte $3_1$ and converts to hydrogen. The oxygen generated at the same time is extracted to the outside of the solid electrolyte $3_1$ by the pumping action of the oxygen pump 3. Detecting and analyzing the electric current passing through the lead wires $3_4$ and $3_5$ makes it possible to know the oxygen content in the metal by referring to the mass of the dropped sample. In the test, the vapor which will be generated during melting may be captured through cooling by the water jacket 12.

Figure 3:
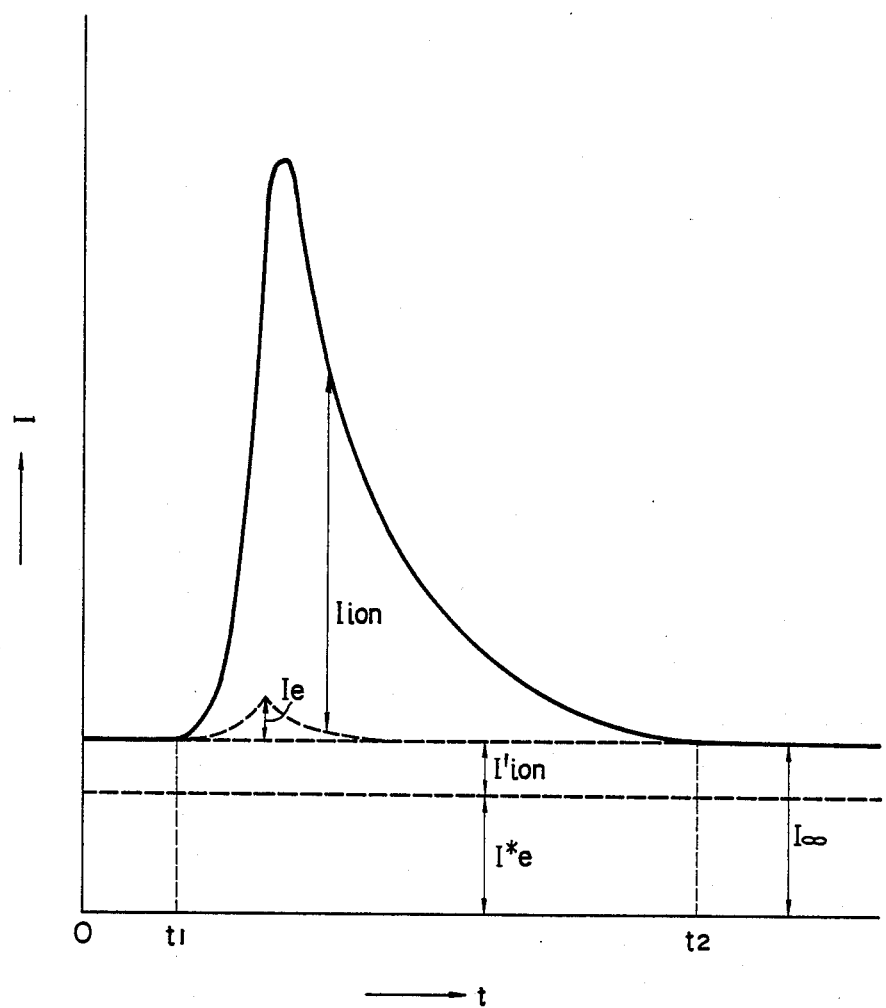
FIG. 3 is a graph showing the relationship between elapsed time and an electric current generated in an oxygen pump in one oxygen analyzing method in accordance with the present invention.

FIG. 3 shows the variation with time t of an electric current I passing through the solid electrolyte $3_1$, which corresponds to the current passing through the lead wires $3_4$ and $3_5$. A constant electric current $I^*e$, which is independent of time t and corresponds to the voltage $E_2$, always passes through the solid electrolyte $3_1$. The ionic current due to the oxygen released from the solid electrolyte $3_1$ is independent of time t and can be considered constant under the above-mentioned conditions. Also, the ionic current due to the extraction of the oxygen having leaked a little into the closed gas flow path 1 from the atmosphere does not depend on time and may be considered constant. Accordingly, the current passing through the solid electrolyte $3_1$ throughout the measurement can be expressed as follows:

$$I\infty = I^*e + I'ion$$

where $I'ion$ is the ionic current passing throughout the measurement.

Where the sample is charged under this state and oxygen is released, the electric current suddenly rises after a time $t_1$. However, it returns to the initial value after a time $t_2$ together with the pumping-out of the oxygen by the oxygen pump 3. Where an average oxygen ion transfer rate is expressed by $\bar{t}$ion, the following equation will theoretically be followed:

$$\bar{t}\text{ion} = \text{Iion}/(\text{Iion} + \text{Ie})$$

where,

Iion is the ionic current passing through the oxygen pump 3 due to the oxygen released from the sample 13 when the released oxygen is extracted from the closed gas flow path 1, and Ie is the electric current due to the ionic current Iion.

When the oxygen pump 3 is operated under the condition of $\bar{t}$ion = 1, the entire quantity of the current which has increased from the constant current $I\infty$ can be considered the current due to the oxygen released from the sample 13. The quantity of electricity Qion due to the ion current Iion is expressed as follows:

$$\begin{aligned} Q\text{ion} &= X \cdot 2F/M \\ &= \int_{t_1}^{t_2} I\text{ion}\, dt \\ &= \int_{t_1}^{t_2} (I - I_\infty)\, dt \end{aligned}$$

where, X is the weight of oxygen (g) released from the sample 13, F is Faraday's constant and M is the atomic weight of oxygen. From the above equation, the oxygen volume which was contained in the sample can be determined. More precisely, an electric current I'e related with I' ion is included, but I'e is also constant provided that I'ion is substantially constant. Therefore, I'e has no influence on the above-mentioned analysis. In addition, I'e can be neglected comparing with I'ion, so long as the oxygen pump 3 is used under the condition of $\bar{t}$ion = 1. This is why I'e is not shown in FIG. 3.

Though, in the above embodiment, the carrier gas employed is argon gas containing hydrogen gas, the carrier gas may be 0.01–100% carbon monoxide gas or carbon dioxide gas, or further may be argon gas containing other reducing gas or argon gas alone. The above argon gas may be substituted with another inert gas such as nitrogen gas or helium gas.

The above analysis arranges the ammeter between the lead wires $3_4$ and $3_5$. However, the arrangement may be modified such that a coulomb-meter is connected to the ammeter in series to measure the quantity of electric charge for the analysis. Where such an arrangement is adopted, the ammeter is not necessary by using a coulomb-meter in which the quantity of electricity due to the constant current $I\infty$ can be subtracted.

In the above embodiment, a voltmeter is connected to the lead wires $3_6$ and $3_7$ therebetween so that the electromotive force of the oxygen pump can be read anytime. However, the arrangement of the voltmeter is optional, because the electromotive force may be checked only when it is necessary.

In the present invention, a potentiostat may be adopted instead of the variable direct current power source. The potentiostat is connected to the lead wires $3_4$, $3_5$ and $3_6$, $3_7$. At least one means selected from the means for measuring current and the means for measuring the quantity of electricity is connected to the lead wires $3_4$ and $3_5$ therebetween. The voltage applied to the lead wires $3_4$ and $3_5$ may be controlled by the potentiostat so that the electromotive force between the lead wires $3_6$ and $3_7$ which is fed back to the potentiostat be a constant specific magnitude.

If errors in the measurement can be tolerated to a certain extent, the lead wires $3_6$ and $3_7$ can be moved to leave only lead wires $3_4$ and $3_5$. In such a case, the direct current voltage applying means and at least one means selected from the means for measuring electric current and the means for measuring the quantity of electricity are connected to the lead wires $3_4$ and $3_5$ therebetween. A voltmeter, if necessary, may be connected in parallel to the variable direct current power source.

The above description concerns the measurement of the oxygen content in metals. However, according to the present invention, the oxygen content in metal compunds, metalloids or gases can be measured in the same way. In the measurement of gases, a sample-introducing means capable of charging a specific volume of gas sample should be employed. The sample-melting furnace is not necessary.

The samples which can be measured by using the oxygen analyzer or the oxygen analyzing method according to the present invention include the following: metals such as copper, indium, lead, iron, nickel, cobalt, tin and gallium; alloys of the above metals; metal compounds such as oxides or nitrides of the above metals; metalloids such as selenium and tellurium; and almost any gas.

Next, using the device shown in FIG. 1, typical samples were selected for measurement of the oxygen content therein. The measurement results were as follows:

EXAMPLE 1

Figure 4:
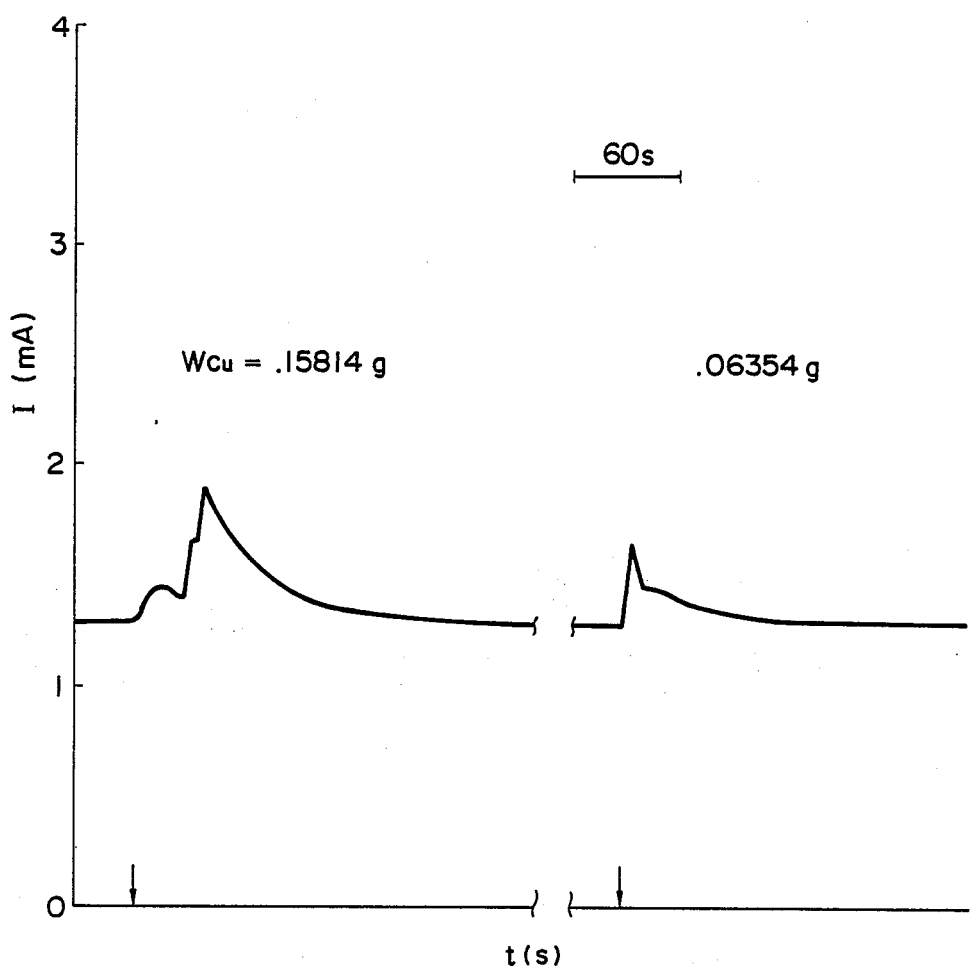
FIG. 4 is a graph showing the relationship between elapsed time and an electric current generated in the oxygen pump in the case of a measurement of the oxygen content in copper.

A copper sample 13 was used for the measurement. FIG. 4 shows a typical relationship between the current I (mA) passing through the oxygen pump 3 and elaped time, on two different samples. In FIG. 4, the mark ↓ indicates the time at which the sample was charged into the sample-melting tube-like chamber 9 of the closed gas flow path 1. One of the samples contained 0.15814 g of copper and the other contained 0.06354 g of copper. These samples consisted of 2 mm diameter copper wires with a purity of 99.998% weight, that is, with impurities of only 0.002% in weight. The temperature in the sample-melting furnace 10 was set at 1200° C. The voltage applied to the oxygen pump 3 was 1.4 V and the temperature in the oxygen pump 3 was 800° C. Argon gas with 0.0942% hydrogen gas was used as the carrier gas. The flow rate of the carrier gas in the closed gas flow path was set at 1 liter/min.

Following the charging of the sample, the current I was rapidly increased due to the oxygen released from the sample. The current I vs. time curve for a relatively large volume of copper turned out rather complicated because the melting point of copper is relatively high. In each measurement the increased electric current dropped to the original current $I\infty$ before the sample-charge within 3 minutes.

Figure 5:
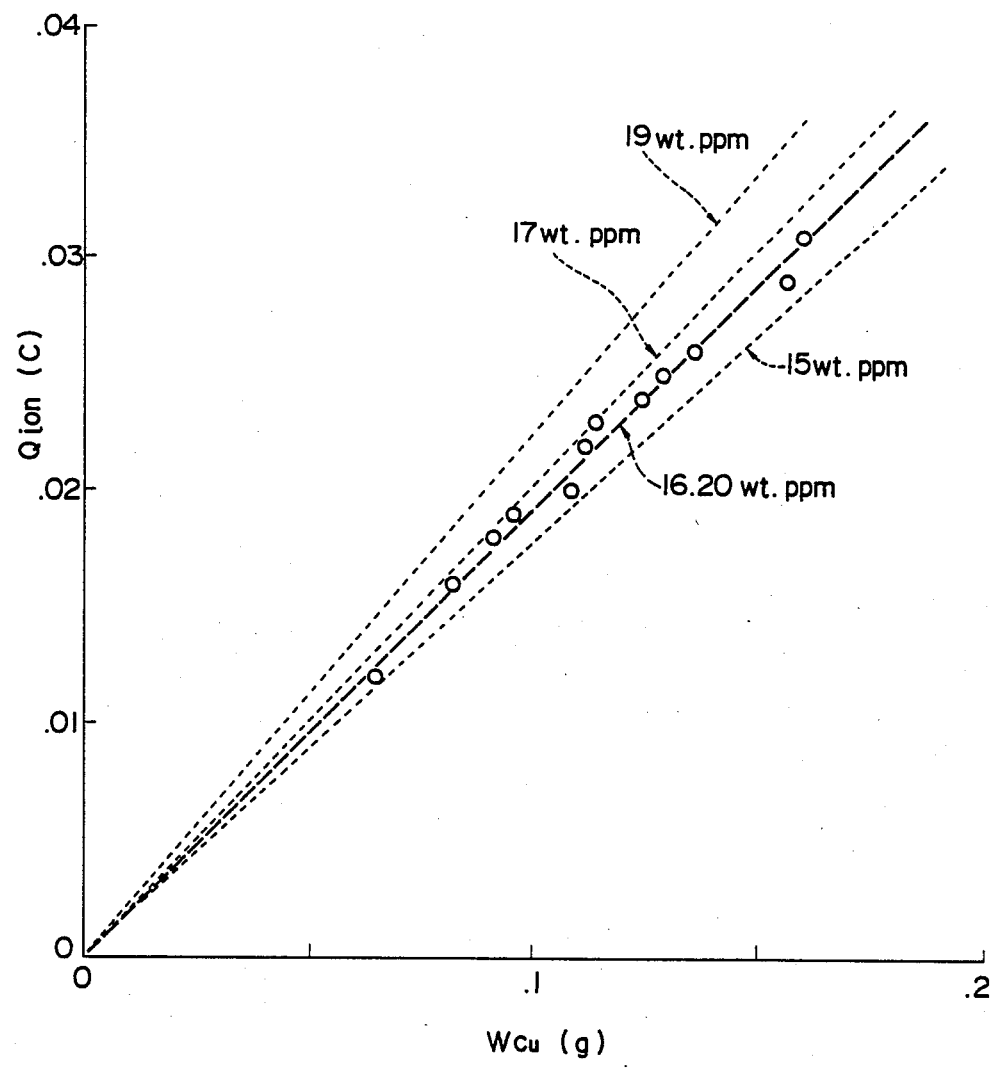
FIG. 5 is a graph showing the relationship between the oxygen weight in the copper and the quantity of electricity needed for the discharge of the oxygen, obtained from the measurement results shown in FIG. 4.

The value of Iion was calculated from the measured value of I and $I\infty$ and therefrom the quantity of electricity Qion due to Iion was calculated. The oxygen weight can be calculated from Qion and the oxygen concentration in the sample can be measured from the relationship between the sample weight Wcu and the Qion. FIG. 5 illustrates the relationship between Wcu and Qion about various samples with different values of Wcu, which has been plotted in order to confirm the reliability of the measured values. If the oxygen concentrations are uniform with respect to the various samples, the Wcu-Qion relationship should be a straight line passing through the zero point. As shown in FIG. 5, even when the sample size (weight) was changed, the measured values did not deviate from the straight line and a high accuracy measurement was confirmed. The average concentration of the oxygen contained in the samples can be determined from the slope of the straight line passing through the zero point. Measurement in the example gave 16.20 wt.ppm as the average oxygen concentration in the samples. Measurement of the samples using a conventional oxygen analyzer gave, as indicated by a dotted line in FIG. 5, measured values of 17 wt.ppm±2 wt.ppm, that is, with a range from 15 wt.ppm to 19 wt.ppm. Comparison with the results obtained using the conventional device demonstrates that the present invention permits a highly accurate measurement in terms of the absolute value of the oxygen content.

Figure 6:
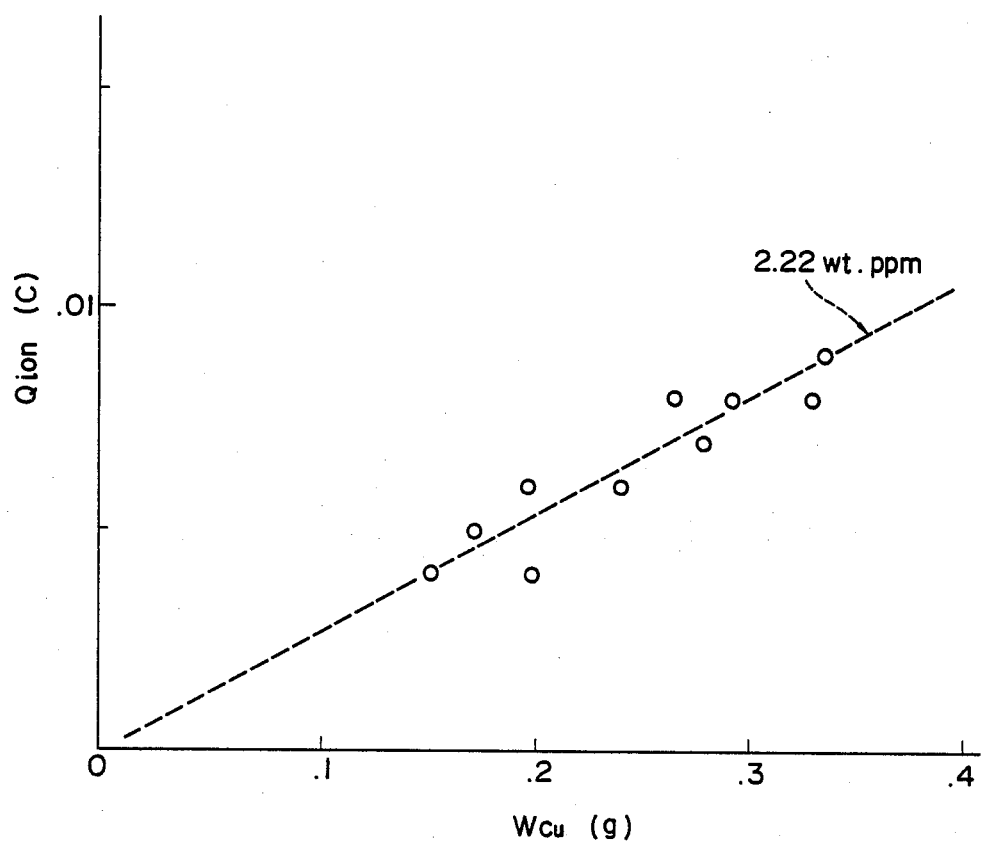
FIG. 6 is a graph showing the relationship between the oxygen weight in the copper and the quantity of electricity needed for the pumping-out of the oxygen, obtained in the measurement of copper with a small content of oxygen using the device of FIG. 1.

FIG. 6 illustrates the results of the measurement of the copper with a small oxygen content performed under the same test conditions as above. The good correlation (i.e. small scatter) of the Wcu-Qion relationship in FIG. 6 clearly shows the accuracy and reliability of the results obtained even with a sample having a low oxygen content.

EXAMPLE 2

Figure 7:
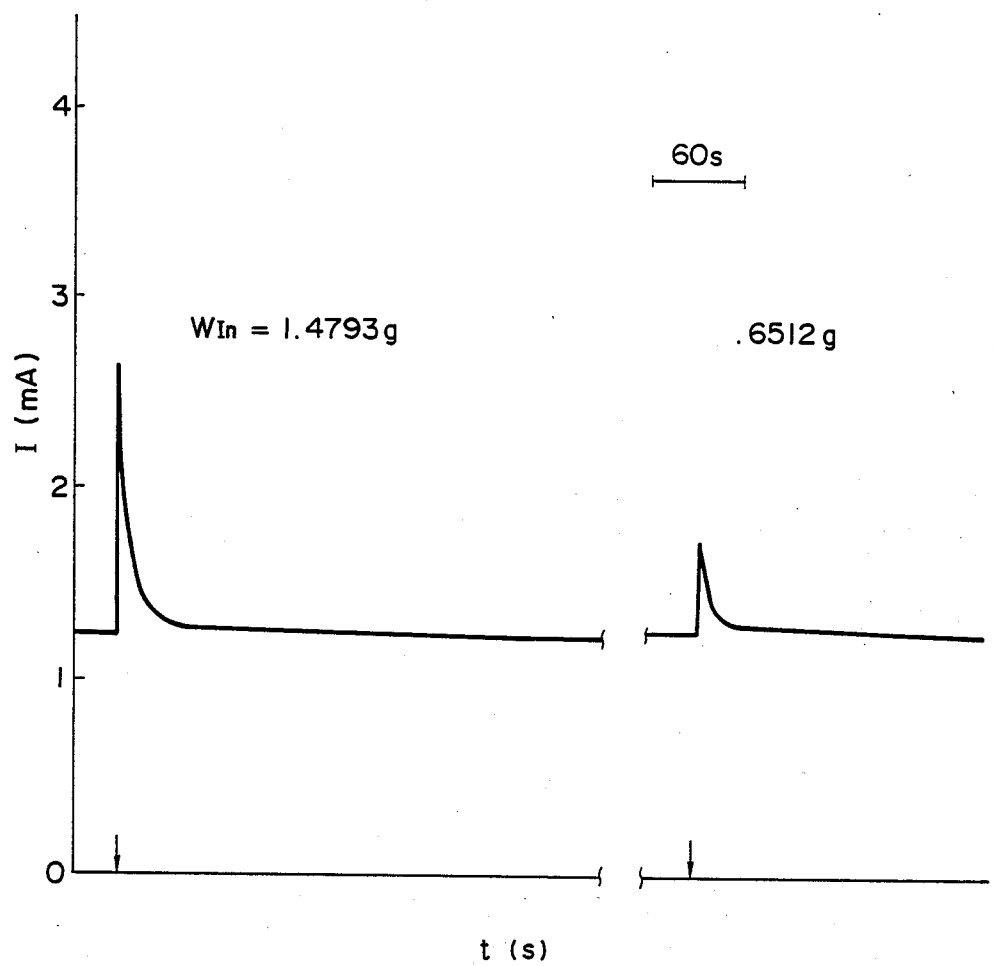
FIG. 7 is a graph showing the relationship between elapsed time and the electric current of the oxygen pump in the case of the measurement of indium using the device of FIG. 1.
Figure 8:
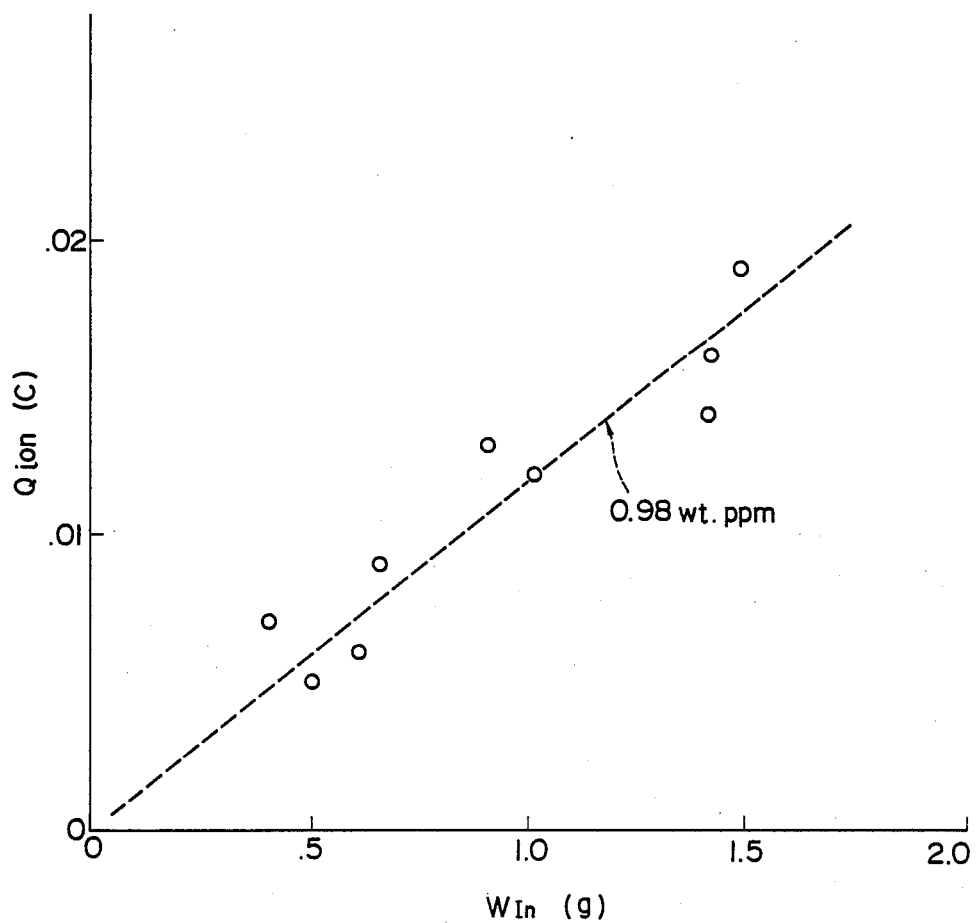
FIG. 8 is a graph showing the relationship between the oxygen weight in the indium and the quantity of electricity needed for the pumping-out of the oxygen, obtained from the measurement results shown in FIG. 7.

In this example, an indium sample was used. The sample-melting furnace was heated to 800° C. Using the same oxygen pump 3 and the same carrier gas as mentioned in Example 1, the oxygen content in the sample was measured. The sample was made by dropping molten indium into water and solidifying it in a form of a tear drop. Since the sample with the form of a tear drop had a very fine surface, it was analyzed as it was. FIG. 7 illustrates the temporary change of the current I in the oxygen pump 3. The melting point of indium is low, and the sample was readily melted in the sample-melting furnace. Therefore, the current I rapidly fell to I∞ after a sharp rise. FIG. 7 shows typical cases where the sample weights WIn are 1.4793 g and 0.6512 g. FIG. 8 plots Qion for samples of different weights. As shown in FIG. 8, the oxygen concentration in the samples was 0.98 wt.ppm.

As is apparent from FIG. 8, the scatter of the data was small and the Qion-WIn relationship had an acceptable correlation value. Thus, with even a sample having a very low oxygen concentration, the measured results are sufficiently accurate and reliable with the present invention.

EXAMPLE 3

In this example, the sample was air. Since the sample was a gas, there was no need for the sample-melting furnace. Therefore, as illustrated by the two-dotted line in FIG. 1, the upstream and downstream portions of the sample-melting furnace 10 on the closed gas flow path had been shut to remove the sample-melting furnace. The filter 14 had also been taken off for measurement. Even without the filter 14, satisfactory data could be obtained.

With respect to the test conditions, the voltage applied to the oxygen pump 3 was 1.2 V and the carrier gas was argon. The remaining conditions of the oxygen pump 3 and the carrier gas were the same as in Example 1.

Figure 9:
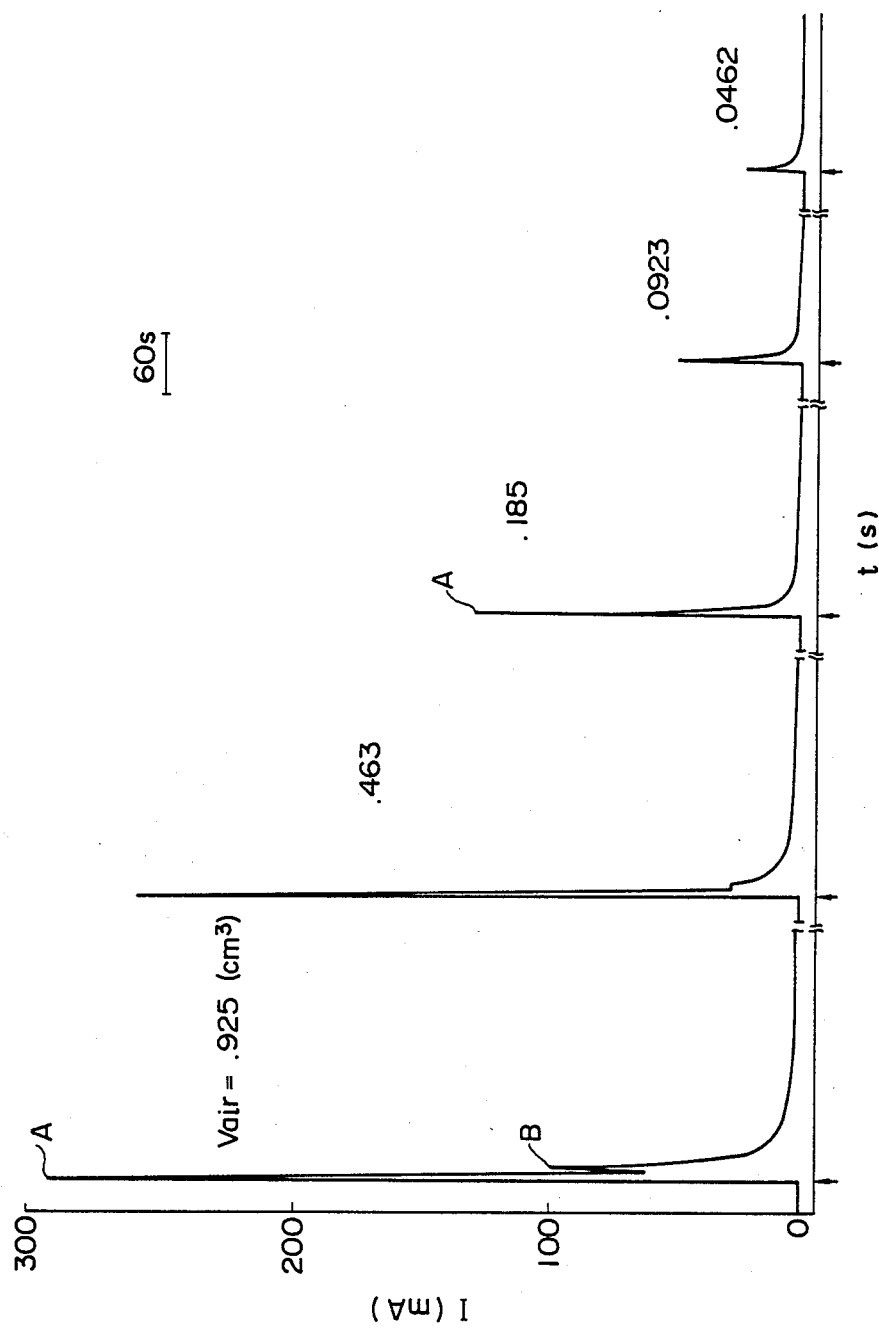
FIG. 9 is a graph showing the relationship between elapsed time and the electric current of the oxygen pump in the case in which the device of FIG. 1 was modified as indicated by the two-dotted line and the oxygen content of air was analyzed.

FIG. 9 illustrates the temporary change of the electric current I in the oxygen pump 3 as measured with different volumes of air introduced into the closed gas flow path 1. FIG. 9 shows the results obtained when the volume of the introduced air was set at 0.925, 0.463, 0.185, 0.0923 and 0.0462 cm$^3$. The sample was introduced into the closed gas flow path 1 by an injector which extends through the rubber plug 7. As shown in FIG. 9, the current I rose rapidly after introduction of the sample. After that, it dropped rapidly and then gradually as time passed, and soon reached the constant current I∞ before the next introduction of the sample. When the value of sample Vair was 0.925 cm$^3$, the curve of the current I had two peaks A and B. The peak A appeared when the sample carried by the carrier gas for the first time reached the oxygen pump 3 and the peak B appeared when the sample after passing the oxygen pump 3 had circulated in the closed gas flow path 1 and for the second time reached the oxygen pump 3.

Figure 10:
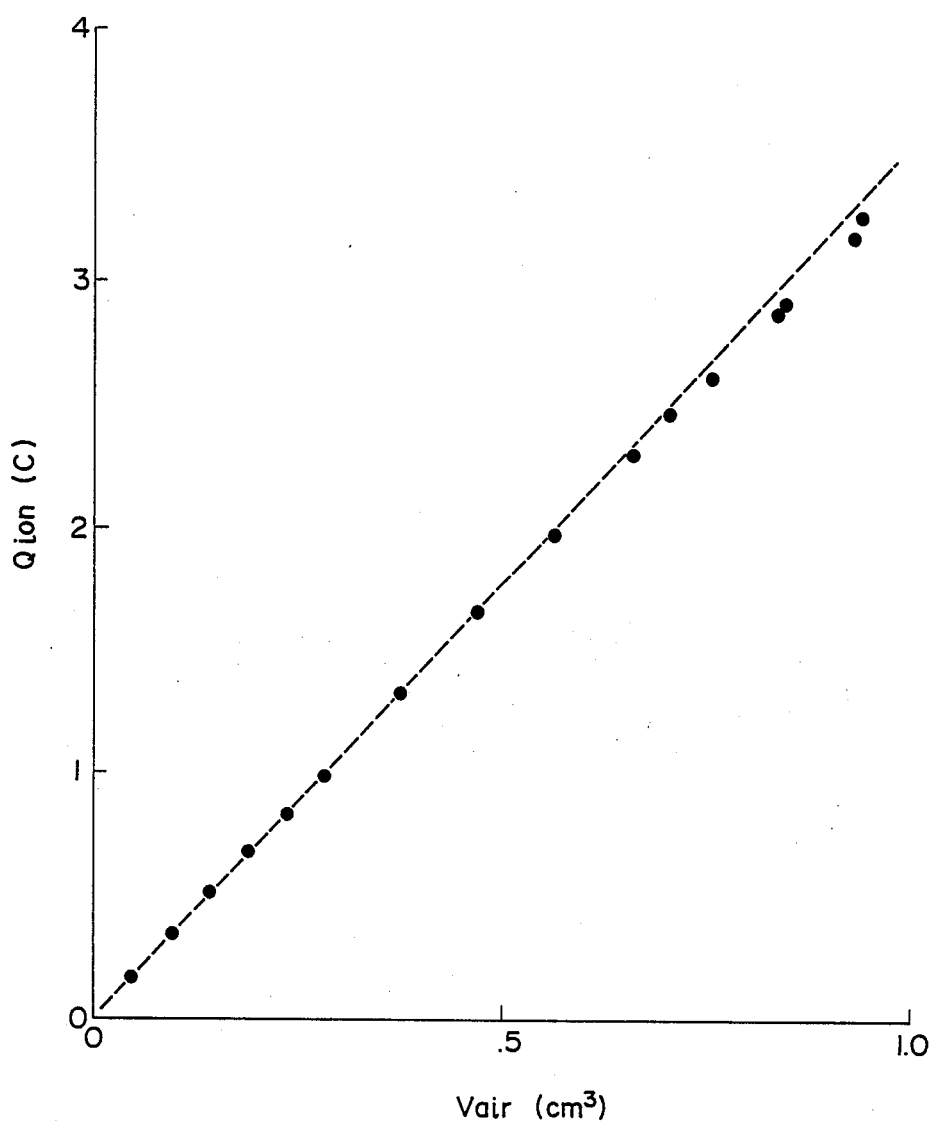
FIG. 10 is a graph showing the relationship between the oxygen volume in the air and the quantity of electricity needed for the discharge of the oxygen, obtained from the measurement results shown in FIG. 9.

Using the data obtained from the above measurement, Qion was plotted against Vair in FIG. 10. The dotted line represents the theoretical value of Qion as calculated from Vair. As is apparent from FIG. 10, the measured values matched the theoretical values well, which demonstrates that the oxygen content even in the gas sample can be measured with high accuracy, independent of the volume of the gas.

Figure 11:
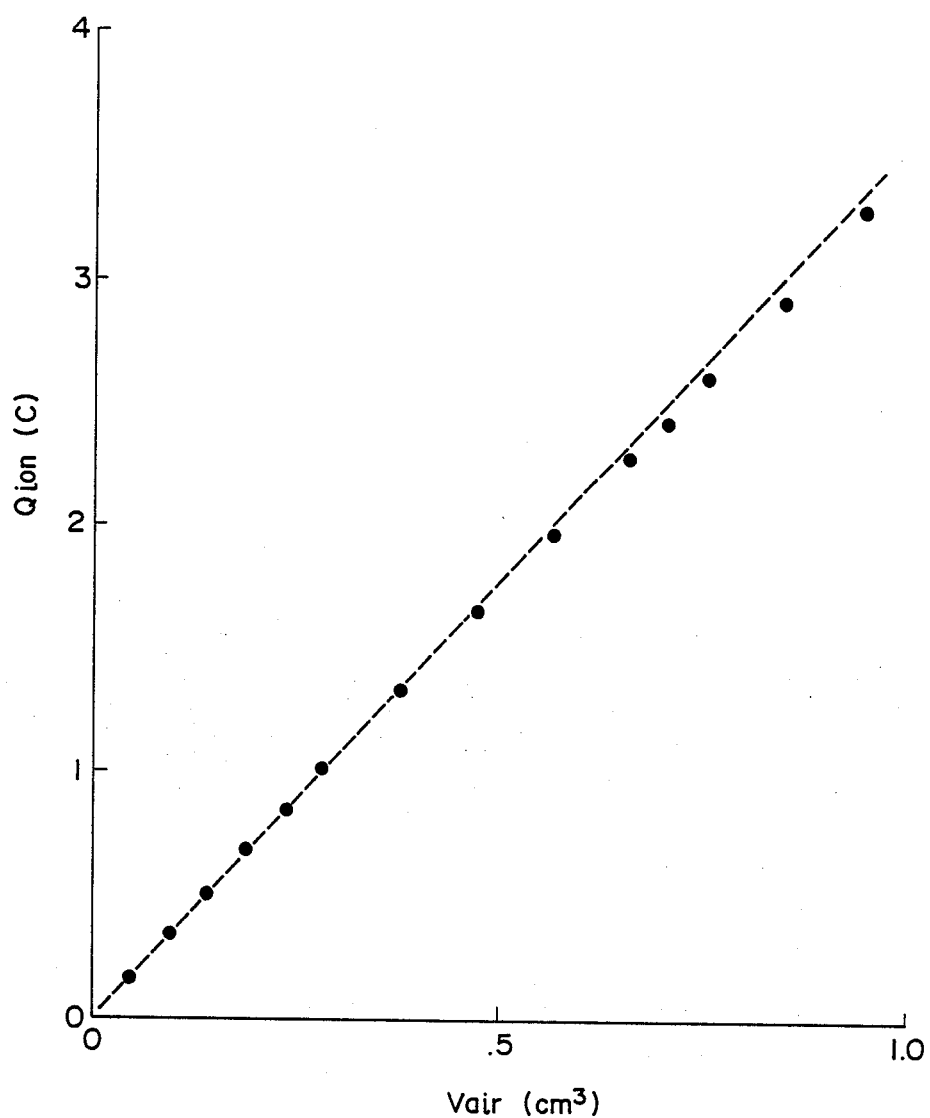
FIG. 11 is a graph showing the relationship between the oxygen volume in air and the quantity of electricity needed for the pumping-out of the oxygen in the case in which the carrier gas was changed to a gas different from the gas in the case of FIG. 9 and the oxygen content of the air was analyzed.

FIG. 11 illustrates the results of measurement where the carrier gas was changed from pure argon gas to argon gas with 0.0942% hydrogen gas as used in Example 1. The dotted line in FIG. 11 indicates the theoretical values similarly to FIG. 10. Comparison between FIG. 10 and FIG. 11 shows that the characteristics of Qion in both figures are nearly identical, and that even when the carrier gas is changed, the absolute value of the oxygen content can be obtained accurately and reliably.

It should be noted that the above examples are representative cases, and as suggested above, a wide variety of samples, carrier gases and measuring conditions can be employed.

What we claim is:

1. A device for analyzing the oxygen content in a sample, comprising:
    a closed gas flow path including a carrier gas inlet port, a vacuum formation port and a sample-introducing port for introducing a sample into said closed gas flow path;
    a pump for circulating a carrier gas along said closed gas flow path;
    an electrochemical oxygen pump for pumping oxygen from said closed gas flow by utilizing a solid electrolyte, said oxygen pump including:
        a heating furnace,
        a cylindrical solid electrolyte, comprising a zirconia material stabilized with one oxide selected from the group consisting of 5-5 mol % of calcium oxide, 6-10 mol % magnesia, and 4-12 mol % yttria housed in said heating furnace, and
        porous electrodes provided inside and outside of said solid electrolyte;
    said circulation pump and said electrochemical oxygen pump being provided in series in said closed gas flow path;
    a sample-melting furnace provided surrounding said closed gas flow path downstream of said sample-introducing port and upstream of said oxygen pump, said sample melting furnace including:
        a sample-melting chamber, and a heating furnace;

a set of lead wires connected to said oxygen pump;

means for applying a direct current voltage connected to said lead wires;

means, connected to said lead wires, for measuring a quantity of electricity necessary for pumping oxygen from said closed gas flow path;

means, provided so as to surround said closed gas flow path downstream of said sample-melting furnace and upstream of said oxygen pump, for cooling gas flowing in said closed gas flow path; and a filter provided in said closed gas flow path downstream of said cooling means and upstream of said oxygen pump.

2. The device of claim 1, wherein said direct current voltage applying means is a direct current power source with a variable voltage.

3. The device of claim 1, wherein siad filter is constructed of a material selected from the group consisting of glass wool, porous glass and ceramics.

4. The device of claim 1, wherein a rectifying tube fabricated of a heat-proof material is placed inside of said solid electrolyte.

5. The device of claim 4, wherein said retifying tube is formed in a capsule-shape and said tube is made into a vacuum.

* * * * *

UNITED STATES PATENT AND TRADEMARK OFFICE
CERTIFICATE OF CORRECTION

PATENT NO.   :   4,786,395

DATED        :   November 22, 1988

INVENTOR(S)  :   Shinya OTSUKA et al

It is certified that error appears in the above-identified patent and that said Letters Patent is hereby corrected as shown below:

Under "Section 102(e) Date: Nov. 7, 1985" in the left hand column on the front page of the patent, please insert the following:

-- [30]   Foreign Application Priority Data

March 7, 1984   [JP]   Japan ...... 59-42110--

Signed and Sealed this

Twentieth Day of February, 1990

Attest:

JEFFREY M. SAMUELS

*Attesting Officer*　　*Acting Commissioner of Patents and Trademarks*